United States Patent
Konno

(10) Patent No.: US 9,907,503 B2
(45) Date of Patent: Mar. 6, 2018

(54) SENSOR SYSTEMS AND METHODS OF USING THE SAME

(71) Applicant: Edwards Lifesciences Corporation, Irvine, CA (US)

(72) Inventor: Mark A. Konno, Laguna Beach, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 335 days.

(21) Appl. No.: 14/436,453

(22) PCT Filed: Oct. 11, 2013

(86) PCT No.: PCT/US2013/064685
§ 371 (c)(1),
(2) Date: Apr. 16, 2015

(87) PCT Pub. No.: WO2014/070424
PCT Pub. Date: May 8, 2014

(65) Prior Publication Data
US 2015/0282751 A1    Oct. 8, 2015

Related U.S. Application Data

(60) Provisional application No. 61/720,766, filed on Oct. 31, 2012.

(51) Int. Cl.
*A61B 5/157*    (2006.01)
*A61B 5/00*    (2006.01)
(Continued)

(52) U.S. Cl.
CPC ............ *A61B 5/157* (2013.01); *A61B 5/1455* (2013.01); *A61B 5/1468* (2013.01);
(Continued)

(58) Field of Classification Search
CPC ...................... A61B 5/1495; A61B 2560/0223
See application file for complete search history.

(56) References Cited

U.S. PATENT DOCUMENTS 5,114,859 A    5/1992 Kagenow
5,145,565 A    9/1992 Kater et al.
(Continued)

FOREIGN PATENT DOCUMENTS

KR    1020090087528    8/2009

OTHER PUBLICATIONS

International Search Report, dated Jan. 23, 2014.
European Extended Search Report for Application 13851833.7, Completed May 31, 2016.

*Primary Examiner* — Puya Agahi
(74) *Attorney, Agent, or Firm* — Moore & Van Allen PLLC

(57) ABSTRACT

Provided are sensor systems and methods for detecting analytes of bodily fluids. The systems can be used to reduce the administration volume of certain compounds and/or fluids during medical monitoring or other procedures by providing a calibration path configured to receive a first fluid, a sample path isolated from the calibration path, the sample path configured to receive a bodily fluid from a subject, and a sensor apparatus comprising at least one sensor selectively positionable between the calibration path and the sample path.

30 Claims, 6 Drawing Sheets

(51) Int. Cl.
  *A61B 5/145*  (2006.01)
  *A61B 5/1495*  (2006.01)
  *A61B 5/1455*  (2006.01)
  *A61B 5/1468*  (2006.01)
  *A61M 5/168*  (2006.01)

(52) U.S. Cl.
  CPC ........ *A61B 5/1495* (2013.01); *A61B 5/14503* (2013.01); *A61B 5/14532* (2013.01); *A61B 5/14546* (2013.01); *A61B 5/6866* (2013.01); *A61M 5/16813* (2013.01); *A61B 5/1451* (2013.01); *A61B 2560/0223* (2013.01)

(56) References Cited

U.S. PATENT DOCUMENTS

| | | | |
|---|---|---|---|
| 5,758,643 A | | 6/1998 | Wong et al. |
| 6,128,519 A | * | 10/2000 | Say ...................... A61B 5/1495 600/309 |
| 2003/0125891 A1 | * | 7/2003 | Dempster ............ A61B 5/1073 702/97 |
| 2009/0018426 A1 | * | 1/2009 | Markle .............. A61B 5/14532 600/365 |
| 2010/0094114 A1 | | 4/2010 | Robinson et al. |
| 2011/0054284 A1 | | 3/2011 | Oviatt |
| 2011/0198241 A1 | * | 8/2011 | Murakami ........... A61B 5/1486 205/792 |
| 2011/0319728 A1 | | 12/2011 | Petisce et al. |
| 2012/0004524 A1 | | 1/2012 | Van Antwerp et al. |

* cited by examiner

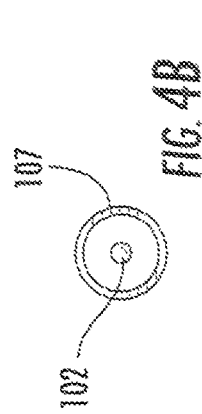
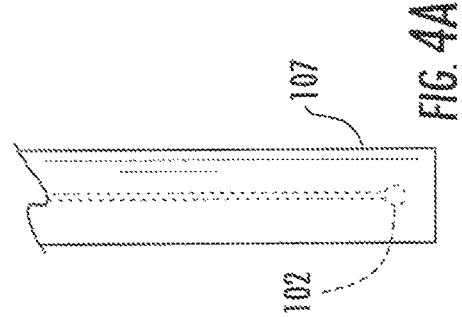
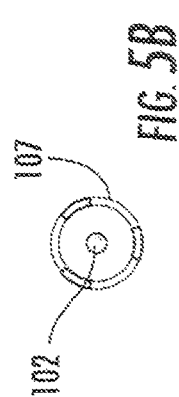
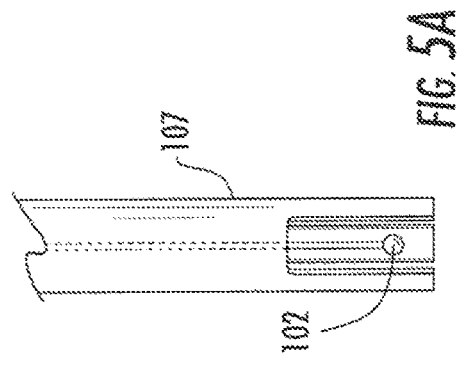
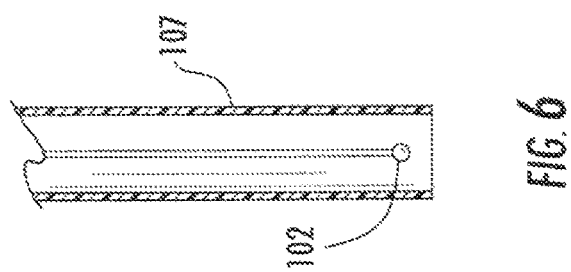
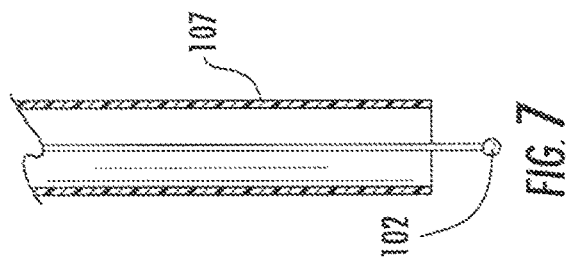
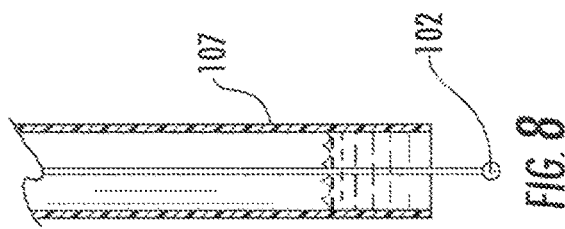

SENSOR SYSTEMS AND METHODS OF USING THE SAME

TECHNICAL FIELD

The present application relates to sensor systems and methods for sensing analytes of bodily fluids. For example, the sensor systems can be used for sensing glucose in blood.

BACKGROUND

Current intravascular sensing devices require calibration and anticoagulants to be infused over the sensor and into the patient's vasculature. Ex-vivo systems require lengthy tubing runs to pull blood away from the patient and the blood must go through numerous valves to prevent calibrants and anticoagulants to be administered to the patient. Many of the ex-vivo systems also require sampled blood to be disposed of via a waste system and not returned to a patient. Sensor systems may therefore undesirably administer volumes of anticoagulants and calibration solutions to patients and/or may temporarily or permanently remove large blood volumes from the patient.

SUMMARY

In a first embodiment, a sensor system is provided, the sensor system comprising: a calibration path configured for fluid communication with a first fluid; a sample path isolated from the calibration path, the sample path adapted to be placed in fluid communication with a bodily fluid of a subject and configured to accept at least a portion of the bodily fluid into the sample path, and a sensor apparatus comprising at least one sensor, wherein the sensor is configured to sense at least one analyte in the bodily fluid, wherein the sensor is selectably moveable between a first configuration wherein at least a portion of the sensor is located in the calibration path and a second configuration wherein at least a portion of the sensor is located in the sample path.

In a second embodiment, a method for sensing one or more analytes in a bodily fluid is provided, the method comprising: positioning an analyte sensor in a first configuration wherein the analyte sensor is positioned in a sample path, the sample path configured in fluid communication with a bodily fluid of a subject, the bodily fluid comprising the one or more analytes; drawing a volume of the bodily fluid into the sample path such that the analyte sensor contacts the bodily fluid and senses the one or more analytes; and positioning the analyte sensor in a second configuration, wherein the analyte sensor is positioned in a calibration path, the calibrant path configured to receive a first fluid.

BRIEF DESCRIPTION OF THE DRAWINGS

FIGS. 4A and 4B are schematic cross sectional illustrations of portions of example sensor apparatuses.

FIGS. 5A and 5B are schematic cross sectional illustrations of portions of example sensor apparatuses.

FIG. 6 is a schematic cross sectional illustration of a portion of an example sensor apparatus.

FIG. 7 is a schematic cross sectional illustration of a portion of an example sensor apparatus.

FIG. 8 is a schematic cross sectional illustration of a portion of an example sensor apparatus.

DETAILED DESCRIPTION

Figure 1:
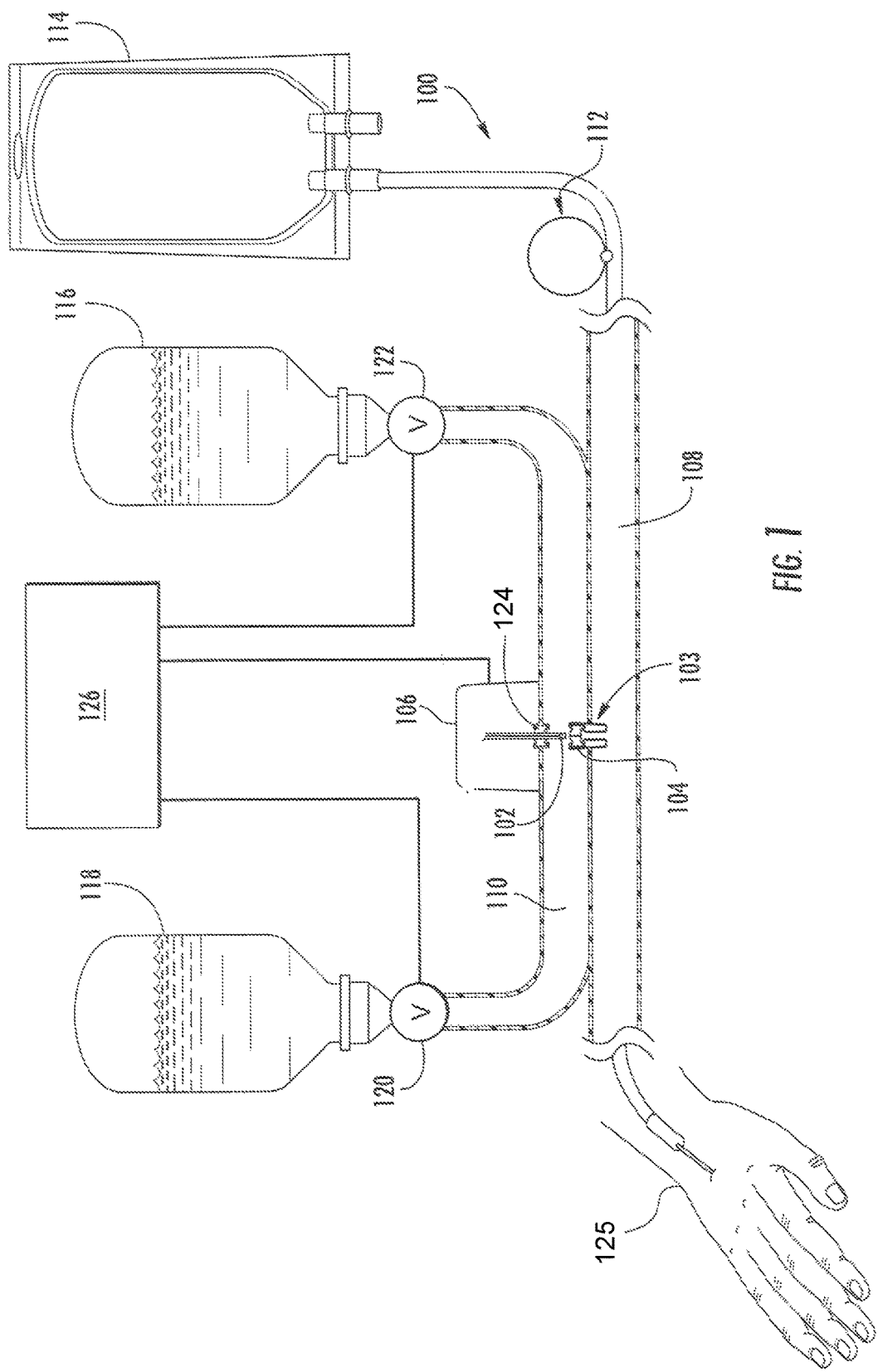
FIG. 1 is a schematic illustration of an example sensor system with the sensor located in a calibration path.

Provided are sensor systems and methods for detecting analytes of bodily fluids. For example, the systems and methods can be used to detect glucose or other analytes in blood or other bodily fluids. The systems and methods can be used to reduce the deliberate or unintentional administration volume of certain compounds and/or fluids during medical monitoring, analyte monitoring, or other procedures. The systems and methods can also prevent temporary or permanent removal of large volumes of bodily fluids from a subject.

An example system comprises a calibration path adapted to contain first fluid and a sample path adapted to be placed in fluid communication with a bodily fluid of a subject. The first fluid can be a flush solution and/or a calibrant fluid. The sample path can receive at least a portion of bodily fluid from the subject. The system further comprises a sensor apparatus. The apparatus includes a sensor that is configured to sense one or more analytes of the bodily fluid. For example, the sensor can sense glucose in blood. The sensor is selectably moveable between a first configuration where at least a portion of the sensor is located in the calibration path and a second configuration where at least a portion of the sensor is located in the sample path.

Optionally, the first fluid comprises calibration fluid and the calibration path can be in fluid communication with a calibration fluid source that comprises one or more calibrants. The calibration path can also be in fluid communication with a second fluid source comprising diluting fluid that optionally comprises anticoagulant, or a fluid that does not comprise calibration fluid. The calibration fluid and the diluting fluid can be optionally mixed in the calibration path, and the sensor, when located in the calibration path, can reside in calibration fluid, diluting fluid, or a mixture of the two.

In the example sensor system, a valve can be disposed between the sample path and the calibration path. The valve is configured to permit movement of the sensor between the first and second configurations during use. For example, in the first configuration the sensor can be initially positioned in the calibration path and then advanced through the valve to its position in the sample path to the second configuration. The sensor, after being positioned in the sample path, can be retracted through the valve to a position in the calibration path, or vise versa.

The valve impedes flow of calibration fluid into the sample path and the flow of physiological fluid into the calibration path. Optionally, the valve comprises a resealable aperture through which the sensor can be moved between the calibration path and the sample path. At least a portion of the sensor apparatus, including the sensor, can be advanced through the valve aperture as the sensor is moved from the calibration path into the sample path. The valve seals about at least a portion of the sensor apparatus when the sensor is positioned in the sample path to impede flow of fluid between the sample path and the calibration path. The valve is configured to reseal and to impede flow of fluid between the sample path and the calibration path when the sensor apparatus, including the sensor, is moved from its position in the sample path into the calibration path.

The example sensor system can further comprise a flow control device configured to regulate flow of bodily fluid, e.g. blood, within the sample path. Optionally, the sample path is further in fluid communication with an infusion fluid source comprising infusion fluid and the flow control device is configured to independently or cooperatively regulate flow of infusion fluid within the sample path. The flow control device can be any flow regulating device such as a valve, a cam, and a pump. If a valve is used, optionally the valve can be a pinch valve. If a pump is used, it can be a volumetric infusion pump, a peristaltic pump, a piston pump or a syringe pump.

The flow control device can be operatively positioned between the sensor and the infusion fluid source. The flow control device can also be selectively activatable to draw bodily fluid from the subject, along at least a portion of the sample path, and into contact with the sensor when the sensor is positioned within the sample path. The flow control device can also be selectively activateable to allow flow of infusion fluid through the sample path.

In the example sensor system, the sensor apparatus further comprises an actuator configured to move the sensor between its position in the calibration path and its position in the sample path. Optionally, the actuator comprises a motor or a solenoid.

The example sensor system can further comprise at least one processing device in operative communication with the actuator and configured to implement activation of the actuator to move the sensor between its position in the calibration path and its position in the sample path.

These and other features and advantages of the present invention will become more readily apparent to those skilled in the art upon consideration of the following detailed description and accompanying drawings, which describe both the preferred and alternative embodiments of the present invention.

The present invention now will be described more fully hereinafter with reference to specific embodiments of the invention. Indeed, the invention can be embodied in many different forms and should not be construed as limited to the embodiments set forth herein; rather, these embodiments are provided so that this disclosure will satisfy applicable legal requirements.

As used in the specification, and in the appended claims, the singular forms "a," "an," "the," include plural referents unless the context clearly dictates otherwise.

The term "comprising" and variations thereof as used herein are used synonymously with the term "including" and variations thereof and are open, non-limiting terms.

Provided are sensor systems and methods for detecting an analyte or analytes in a sample. For example, the systems can be used to detect glucose in blood. The systems can be used to reduce the administration volume of certain compounds, pharmacological agents and/or fluids to patients during medical monitoring or other procedures.

An example system 100 comprises a calibration path 110 adapted to contain a first fluid and a sample path 108 adapted to be placed in fluid communication with a bodily fluid of a subject 125. The sample path 108 can receive at least a portion of the bodily fluid. The system 100 further comprises a sensor apparatus. The apparatus includes a sensor 102 that is configured to sense an analyte in the bodily fluid. For example, the sensor 102 can sense glucose in blood. The sensor 102 is selectably moveable between a first configuration where at least a portion of the sensor is located in the calibration path 110 and a second configuration where the sensor is located in the sample path 108. During sensing and calibration, the calibration path and the sample path can remain substantially isolated as to fluid flow therebetween.

Referring to FIG. 1, an example sensor system 100 comprises a sample path 108 and a calibration path 110. The sample path 108 can be used to access bodily fluids of a subject 125.

One example of a bodily fluid that can be accessed by the sample path 108 is blood. Other bodily fluids can be sensed, such as interstitial fluid, or a mixture of bodily fluids, e.g., blood and interstitial fluid. The sensor system can further comprise a sensor 102 adapted to sense analytes in the bodily fluid. One example analyte that can be sensed or measured is glucose. Other analytes, alone or in combination, can be sensed, for example, using a plurality of sensing elements on sensor 102.

In the described systems and methods, the sensor 102 can be positioned in the sample path 108 for contacting the bodily fluid and for sensing the analyte. Following sensing of the analyte in the bodily fluid, the sensor can be positioned in the calibration path 110 for calibration. The sample path and the calibration path are fluidly isolated such that fluid does not freely flow between the paths. In this way, administration of fluid from the calibration path to the subject can be substantially prevented. In an exemplary embodiment, the sensor 102 can first be positioned in the calibration path 110 for calibration. Calibration can also include sensor break-in, where "break-in" relates to the time (after introduction to either the calibrant or the sample from subject) during which the sensor's signal is becoming or has become substantially representative of the analyte concentration being detected and/or monitored. In this exemplary embodiment, following calibration and/or break-in of the sensor, the sensor is positioned in the sample path for sensing (and/or determining) analyte in the bodily fluid. This sequence can be reversed or repeated. Optionally, during first use of the system for a subject, the sensor can be introduced to the sample path for initial and/or additional break-in.

To access blood, the sample path 108 can be configured, for example, as a catheter having a lumen with an opening in the subject. The catheter can be inserted into an artery or vein of the subject such that the lumen of the catheter is in fluid communication with the subject's vasculature. In one aspect, the sample path is a very small diameter tube (or catheter) with correspondingly sized lumen to minimize the amount of sample withdrawn from the subject. The sample path can comprise any line of a catheter or tubing, which can be single or multi-lumen. In the case of a multi-lumen catheter, any lumen configured to draw a bodily fluid into that lumen can act as a sample path. Similarly, each sample path can be optionally attached to a source of infusion fluid, as described below. A flow control device can be used to introduce blood and/or infusion fluid into the sample path, e.g., by drawing blood from the subject into the catheter lumen or infusion fluid from an external source.

The flow control device can include a variety of fluid flow-regulating devices. Optionally, the flow control device includes one or more valves, such as, but not limited to, linear and non-linear roller valves, linear and non-linear pinch valves, bi-directional valves (either linear or non-linear), peristaltic rollers, cams, combinations thereof, and the like. The flow control device can also comprise a variety of flow regulating devices, such as, but not limited to, cams, pumps, and the like.

Figure 2:
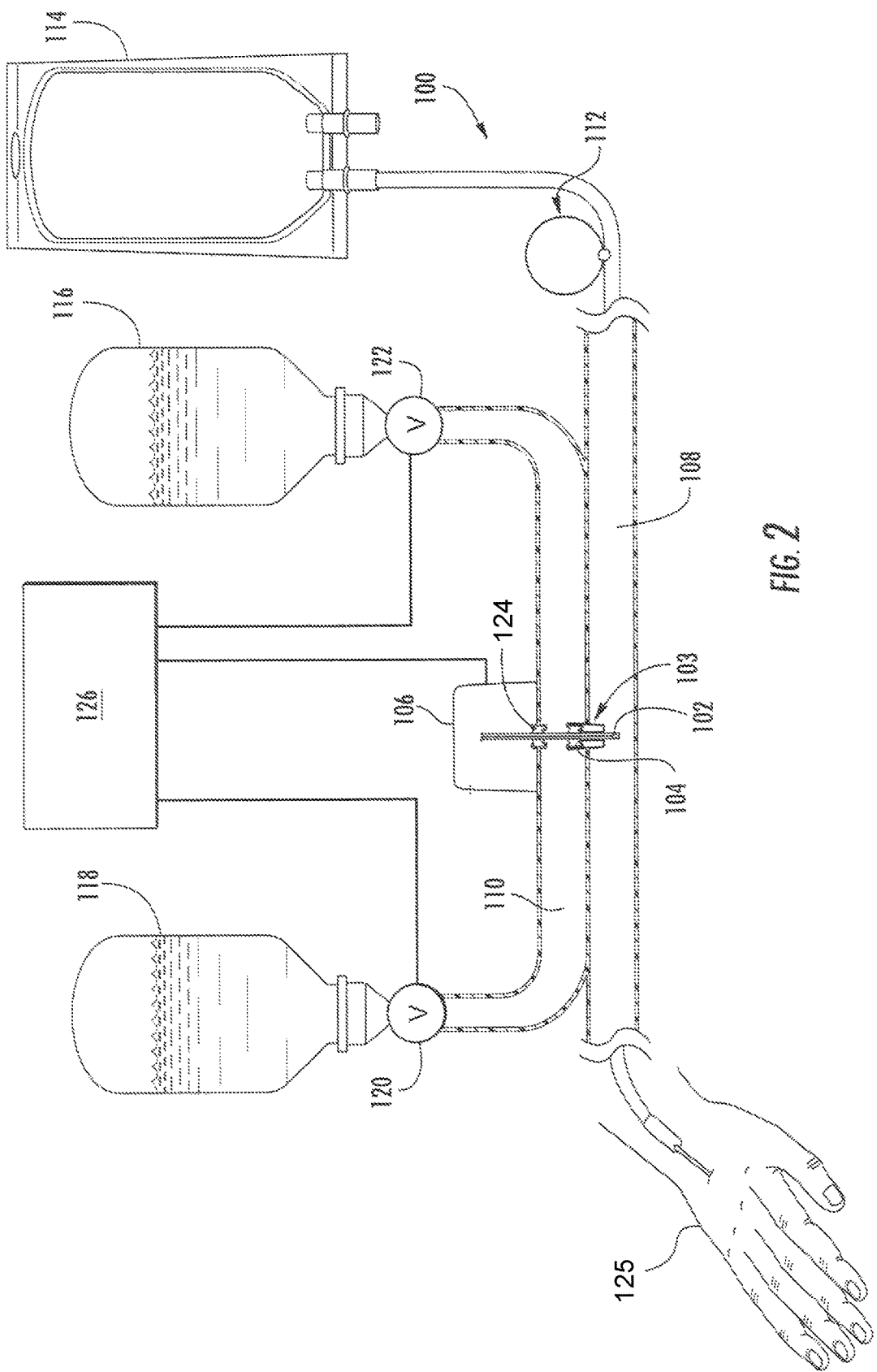
FIG. 2 is a schematic illustration of an example sensor system with the sensor located in a sample path.

As shown in FIGS. 1, 2 and 9, optionally, the flow control device is a rotating pinch valve 112 that has first and second positions. The valve 112 can move between the two positions, for example, backward and forward, and thereby move bodily fluids in and out of the catheter. A bodily fluid sample can therefore be drawn from the subject into the sample path 108, to contact a portion of the sensor 102 that is used to sense an analyte, and then pushed back into the subject, by movement of the valve between the first and second positions.

Figure 9A:
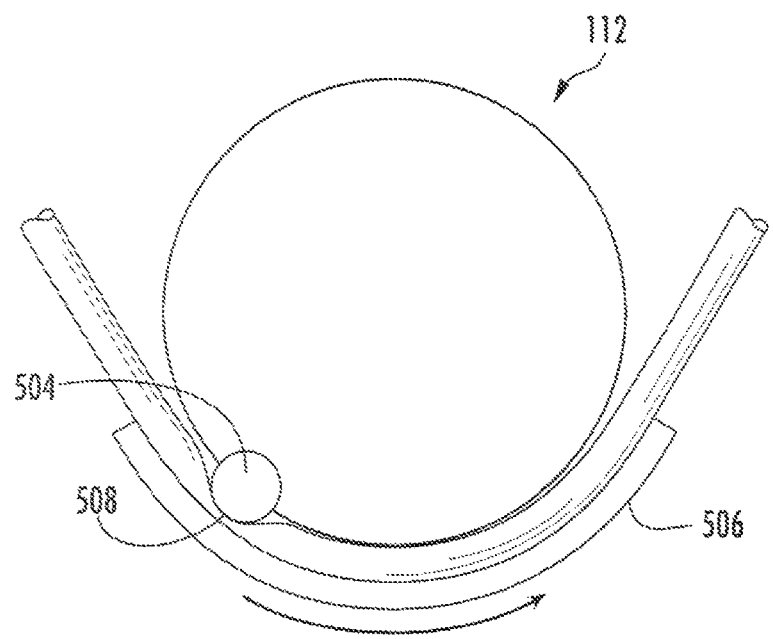
FIGS. 9A and 9B are schematic illustrations of an example valve for use as flow control device in the example system of FIGS. 1 and 2.
Figure 9B:
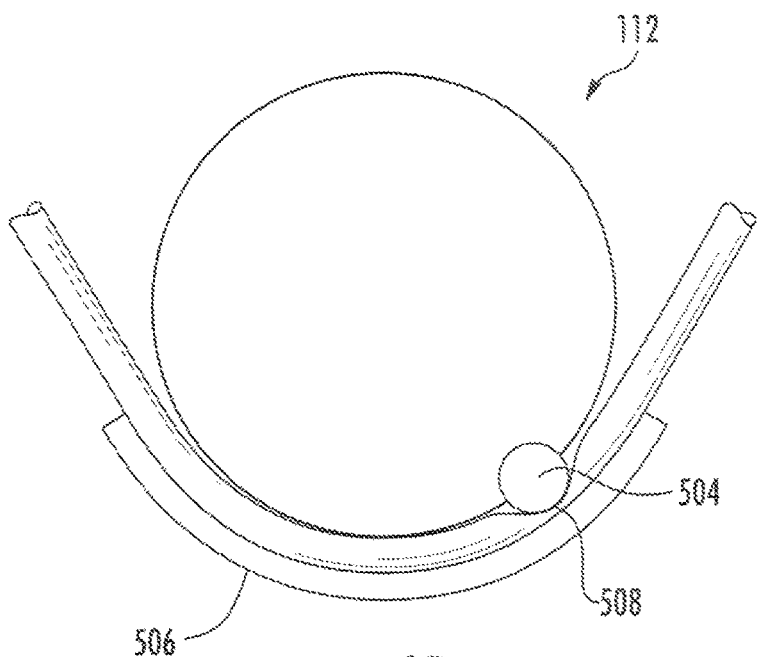

Referring to FIGS. 9A and 9B, the flow control device, such as the valve 112, can be configured such that a tube in fluid communication with the sample path 108, or a portion of the sample path itself 108, is threaded between the first and second structures (504 and 506 respectfully) (e.g., between the roller and the surface against which the roller presses) is compressed substantially closed. For convenience, the compressed location 508 on the sample path 108 is referred to herein as the "pinch point."

Optionally, the flow control device is configured such that the pinch point is moved along the sample path, either closer to or farther from the subject. As the pinch point is moved closer to the subject, the sample path is progressively compressed, causing fluid to be pushed into the subject's vascular system at the site where the sample path is implanted in the subject. Conversely, as the pinch point is moved away from the subject, the portion of the sample path on the subject side of the pinch point progressively expands, causing sample (e.g., blood) to be drawn up into the sample path lumen. Optionally, the flow control device is configured such that the pinch point is substantially stationary and the first and second structures selectively compress the sample path at the pinch point (e.g., the tube is either pinched fully closed or is fully open), which either stops or allows the flow of fluid through the sample path lumen. This configuration can be used to flush the sample path 108 using fluid from the fluid source 114.

Thus, in some aspects, the sensor system is configured to allow a sample (e.g., blood) to contact the sensor 102 using the flow control device. The flow control device is configured to draw back (or take-in) a sample (e.g., blood) from the subject. Optionally, the flow control device is configured to take up a sufficient volume of sample such that at least the sensor's 102 sensing portions are contacted by the sample. Optionally, a sample volume of from about 1 µl or less to about 2 ml or more is taken up into the sample path 108. Optionally, the sample volume is from about 10 µl to about 1 ml. Optionally, the sample volume is from about 20 µl to about 500 µl. Optionally, the sample volume is from about 25 µl to about 150 µl. Optionally, the sample volume is from about 2 µl to about 15 µl. Other sample volumes can be used.

As described above, and with reference to FIGS. 1 and 2, by activating the fluid control device, such as the valve 112, blood can be drawn through and along the sample path 108.

In the system herein described, the sample path can also be configured such that the sample path is placed in fluid communication with a source of infusion fluid 114 as further described below. The infusion fluid can comprise any fluid which may be infused into a subject during a medical procedure or monitoring procedure. Such fluids include lactated Ringers solution, saline, or other medical solutions and fluids known to those skilled in the art.

In one aspect, the sample path is configured such that the sample path is placed in fluid communication with a source of infusion fluid 114, where the fluid control device, such as the valve 112, regulates flow of an infusion fluid through the lumen of the sample path. In one aspect, the infusion fluid is introduced to the sample path in a direction opposite that of the direction of sample flow from the patient. Optionally, when the valve 112 is activated to draw a bodily fluid, such as blood, into the sample path from the subject, the valve 112 is configured to prevent flow of infusion fluid from the infusion fluid source 114 through the sample path and into the subject. Thus, the valve 112 can regulate flow of bodily fluid, e.g. blood, and infusion fluid, e.g. Ringers solution, through the sample path. In another aspect, the valve 112 can directionally regulate the flow of bodily fluid, e.g. blood, and that of the infusion fluid. In yet another aspect, the valve 112 can bi-directionally regulate the flow of bodily fluid, e.g. blood, and that of the infusion fluid.

By way of example, bi-directional fluid control can allow blood drawn into the sample path to be flushed back into the subject using the infusion fluid. Optionally, gravity can be used alone or in combination to urge the infusion fluid though the sample path by positioning the infusion fluid source above the termination of the sample path in the subject.

Again referring to FIGS. 1 and 2, the example sensor system 100 can further comprise a calibration path 110. Similar to the sample path, the calibration path can be a tubular conduit having one or more lumens for the passage of fluid. Instead of being placed in fluid communication with the subject 125, however, the calibration path 110 is configured to accept flush fluid, which may further include a calibrant ("calibration fluid") from a calibration fluid source 118 and/or an anti-coagulant. Thus, in one exemplary embodiment, the calibration path 110 can be configured to accept fluid from a second fluid source 116 that comprises, for example, saline or another fluid that can be mixed with the calibration fluid within the calibration path 110, and/or an anti-coagulant for contacting the sensor during its residence in the calibration path. In this aspect, fluid in the calibration path can comprise anti-coagulant additives, such as heparin, heparin derivatives, non-heparin compounds, etc., such compounds being useful to contact the sensor and provide it with anti-coagulant properties while in the calibration path and/or properties that will remain when exposed to the sample path, and thus, minimize or eliminate the need to directly introduce such compounds into the sample path and/or subject, or the need coat, layer, infuse, or otherwise provide anti-coagulant properties directly to the sensor. The sensor can be contacted with the second fluid source for a predetermined time interval and then the system can terminate flow of the second fluid source and introduce the flush solution. This process can be repeated FIGS. 1 and 2 show the sample path and calibration path adjacent each other. Other configurations, including, for example, a fluid conduit, T-connector, Y-connector, or similar connector can be used to bring the sample path and calibration path in proximity for manipulation of the sensor 102 between the two paths.

Fluid in the calibration path can comprise one or more calibration or reference solutions, wherein the sensor system is configured to expose the sensor 102 to the one or more reference solution(s) to provide calibration information, such as baseline and/or sensitivity information for the sensor. Optionally, the reference solution includes a known analyte concentration, wherein the sensor system is configured to expose the sensor to the reference solution, and wherein the system is configured to produce a data signal indicative of an analyte concentration in the reference solution during exposure of the sensor to the reference solution. The system can be configured to obtain internal reference values at one or more time points, intermittently, and/or continuously. Although a reference calibration solution can be used to provide an internal reference value, other sensor technologies, such as optical sensing methods, can be used to provide one or more internal reference standards (e.g., of known absorbance, reflectance, fluorescence, etc) to determine baseline and/or sensitivity information.

Optionally, the sensor is a glucose sensor, and the calibration solution contains dextrose or glucose at a concentration of from about 0 mg/dl to about 1000 mg/dl. Optionally, the solution contains from about 50 mg/dl to about 400 mg/dl glucose. Optionally, the solution contains from about 100 mg/dl to about 150 mg/dl glucose. Optionally, the calibrant solution is an isotonic saline solution containing the dextrose or glucose.

As shown in FIG. 1, in a first configuration of the system during use, a valve 120 positioned along the calibration path 110 between the calibration fluid source 118 and the location of the sensor 102 when the sensor is positioned the calibration fluid path, is provided. Ideally, in this first configuration, the sensing portion of the sensor, e.g., that portion containing the sensing chemistry, is positioned within the calibration path and not exposed to or contacted by the sample path or its contents. Thus, although the sensor 102 is shown in FIG. 1 as completely positioned in the calibration path, an alternate configuration is one where the sensor chemistry of the sensor is positioned along the length of the sensor and arranged to be manipulated or introduced between the sample path and calibration path while at least a portion of the sensor is present in both paths while in the first configuration. The valve 120 can regulate flow of calibration fluid through the calibration path 110 for contacting the sensor, which can be for a predetermined time or manually controlled. Similarly, a valve 122 can be located along the calibration path 110 between the second fluid source 116 and the position of the sensor 102 when it is in the calibration path. The valve 122 can regulate flow of fluid from the second fluid source along the calibration path for contacting the sensor, which can be for a predetermined time or manually controlled. By controlling the valves 120 and 122, different mixtures of calibration fluid and the second fluid can be delivered selectively to the sensor 102 when it is located in the lumen of the calibration path. The calibration fluid and the second fluid can be uni-directionally or bi-directionally introduced into the calibration path and to contact, flush, and/or provide anti-coagulation properties to the sensor. One or more flow regulation devices can be used, coupled to the calibration path (not shown), to at least control fluid flow in the calibration path, as discussed herein for the sample path. Flow paths to waste containers (not shown) can also be employed to remove some or all of the contents of the calibration path, either manually or at predetermined time intervals.

The fluid in the calibration path 110 can be isolated from fluid in the sample path 108. In this way, calibration fluid does not enter or flow freely into the sample path 108 and fluid in the sample path 108 does not enter or flow freely into the calibration path. By this isolation, calibration of a sensor 102 can occur in the calibration path 110 without substantial contamination of bodily fluid or other fluids in the sample path. In one aspect, the calibration is improved by subjecting the sensor to a flush, e.g., using the second fluid source, to remove traces of bodily fluid sample present on the sensor, for example, after being in the sample path.

Moreover, sensing of an analyte, e.g. glucose, of bodily fluid, e.g. blood, drawn into the sample path 108 can be accomplished without contamination of the sample path with calibration fluid, or any mixture of fluid contained in the calibration path 110. Also, the isolation between the two paths allows for the sample path 108 to be flushed using infusion fluid from the infusion fluid source 114 without administering a substantial amount of calibration fluid or any mixture of fluid in the calibration path into the subject.

Figure 3A:
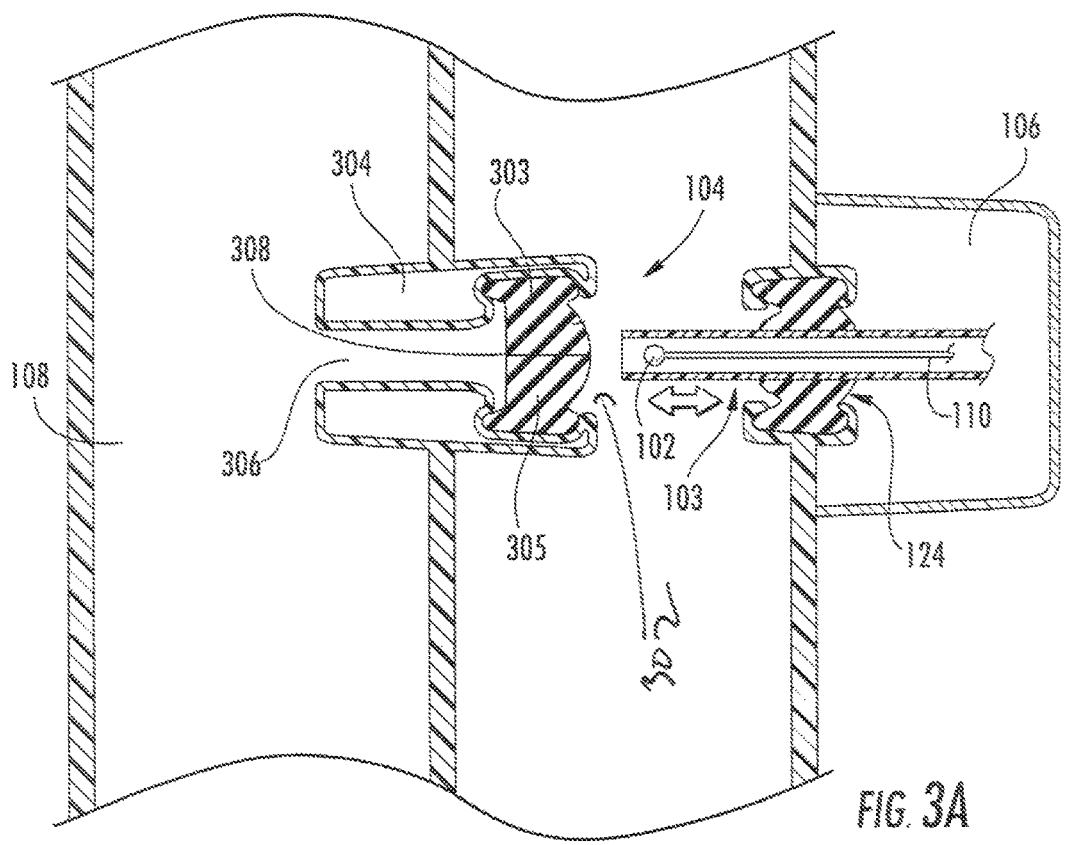
FIG. 3A is a schematic cross sectional illustration of portions of the example sensor system of FIG. 1 with the sensor located in a calibration path.

Referring again to FIGS. 1 and 2, a valve 104 can be positioned between the calibration path 110 and the sample path 108. The valve can comprise a sealable aperture (as further shown in FIGS. 3A and 3B and described below). The sealable aperture impedes the flow of fluids between the calibration fluid path 110 and the physiological fluid path, which is represented by sample path 108.

The valve 104 can comprise a septum 302. The sealing septum has a resealable aperture 308 extending therethrough. The sealing septum can be a thin, molded, sealing septum.

As shown in FIG. 2, in a second configuration, at least a portion of the sensor apparatus 103 can be forced through the sealing septum, which can place a portion of the sensor apparatus, including the sensor 102, into the lumen of the sample pathway. In this configuration, the sensor can be exposed to or contacted by bodily fluids present in the sample path. In this configuration, the sensor can detect, quantify, or qualify one or more analytes of interest present in the bodily fluid of the subject.

Figure 3B:
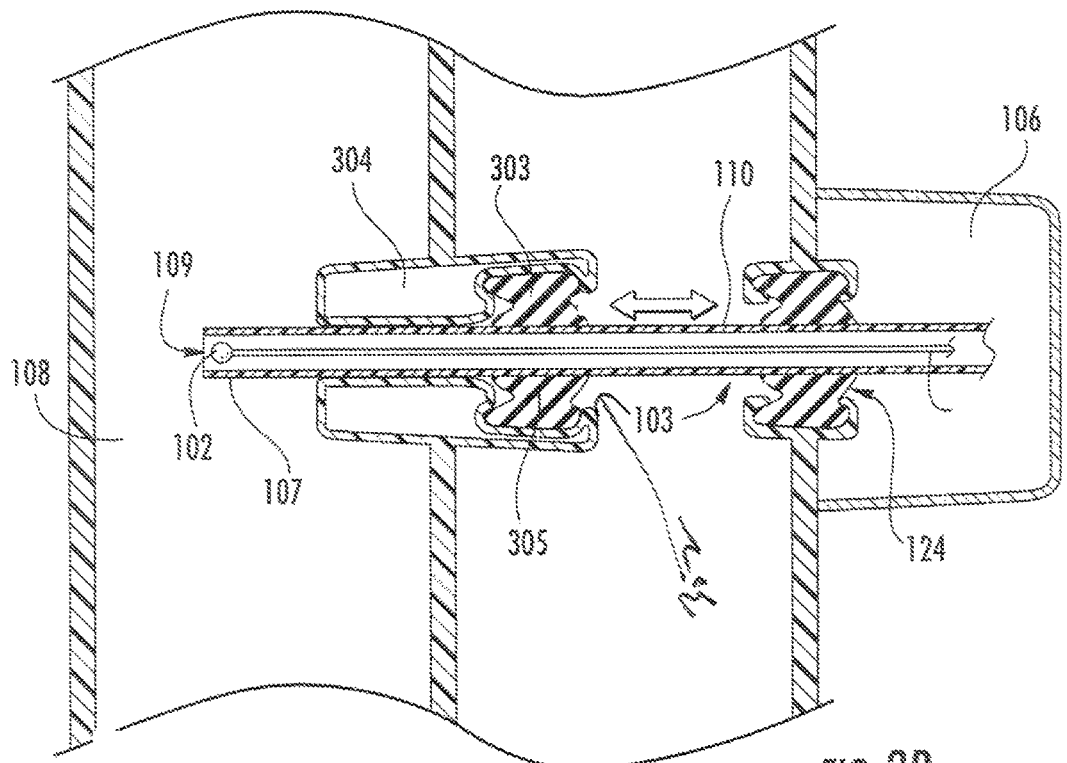
FIG. 3B is a schematic cross sectional illustration of portions of the example sensor system of FIG. 2 with the sensor located in a calibration path.

As shown in FIG. 3B, a sensor apparatus 103 containing sensor 102 can be employed. In an alternate configuration sensor 102 can be used without apparatus 103. As shown in FIG. 3B, at least a portion of the sensor apparatus 103 can be forced through the sealing septum, which thereby places a portion of the sensor apparatus, including the sensor 102, into the lumen of the sample pathway. The resealable septum 302 is optionally positioned in a housing 304 or other multi-tube connector. The septum 302 includes first and second spaced apart structures 303 and 305 respectively. The septum 302 can have a generally cylindrical shape. The septum can be formed of a latex, silicone, urethane, or synthetic rubber material. Alternately, the septum can be formed of a thermoplastic elastomer. The material used for the septum preferably is non-toxic and sterilizable such as by means of radiation, steam, or Ethylene Oxide.

The portion of the sensor apparatus 103 that can be driven through the resealable aperture can include a conduit 107. The conduit 107 can be resilient enough to be forced through the valve while protecting the sensor from damage during the advancing or retraction process. Optionally, the sensor 102 is housed within the lumen of the conduit 107 and the portion of the sensor which contacts bodily fluid and senses an analyte in the bodily fluid is positioned near the tip of the conduit where there is at least one opening 109 for the bodily fluid to access the conduit and the sensor.

The conduit can be configured, similar to the sample path, to draw up a portion of the bodily fluid through the opening 109 and into the lumen of the conduit. The sensor can be positioned such that fluid drawn into the conduit contacts the sensor allowing for an analyte to be sensed. Optionally, the conduit 107 or a tube in fluid communication with the conduit can be configured for use with a valve similar to the pinch valve 112 so that bodily fluid can be drawn into the conduit when the tip portion of the conduit is positioned within the sample path. Similarly, calibration fluid can be drawn into the conduit to bathe the sensor when the conduit is positioned within the calibration path. The drawing up of fluid, bodily fluid or calibration fluid, into the conduit 107 is shown schematically in FIG. 8.

Referring to FIGS. 4A and 4B, the sensor 102 can also be placed in close enough proximity to the tip of the conduit 107 such that fluid, bodily or calibration, contacts the sensor without actively drawing fluid up into the lumen. Referring to FIGS. 5A and 5B, the tip of the conduit can be perforated or notched to better allow contacting of the sensor 102 with bodily or calibration fluid. In another embodiment, sensor 102 is integrated with conduit 107, for example, in an interior or exterior portion of conduit 107.

FIGS. 6 and 7 show examples of the system 100 where the sensor onto is extended or withdrawn into the conduit 107 for sensing of bodily fluid in the sample path 108 or for calibration in the calibration path 110. In this regard, the sensor can be coupled to an actuator which can move the sensor relative to the conduit. In other examples (not shown), the sensor itself is configured of a material suitable to be extended and withdrawn through the valve without damage. In still other examples, the sensor is protected by a hood device (not shown) that pushes through the aperture an allows access of the sensor to bodily or calibration fluid.

When the sensor apparatus is withdrawn into the calibration path 110 from the sample path 108, the aperture 308 can reseal with enough force that fluid flow is impeded or prevented between the calibration path and the sample path.

By impeding or preventing the flow of fluid between the corresponding paths, the valve 104 can prevent a substantial amount of fluid from passing between the lumens of the respective path. The valve 104 can be penetrated, however, by the sensor apparatus 103, conduit 107, and/or the sensor 102. The sensor apparatus 103 can be selectively advanced from a first position in the lumen of the calibration path 110 while in the first configuration to a second position in the lumen of the sample path 108 while in the second configuration.

While in the second configuration, the sensor 102 is positioned in sample path 108 for sufficient time to sense an analyte, thereafter it can be retracted from the sample path, through the valve 104, and back to the first configuration with the sensor 102 positioned in the calibration path 110. In the retracted first position, with the sensor in the lumen of the calibration path 110, the valve 104 is sealed and fluid is not substantially exchanged between the calibration path 110 and the sample path 108. In this first position, the sensor is calibrated in the calibration path 110, which is in fluid isolation from the sample path 108. In the advanced or second position, the sensor sits in the lumen of the sample path 108. In this position, the sensor can be used to sense an analyte of a bodily fluid draw into the sample path. Infusion fluid can be passed over the sensor and into the subject while in the second configuration. The infusion fluid can be presented to the sensor in a uni-directional manner so as to act to cleanse the sensor before retraction into the calibration path.

The sensor is configured to measure the concentration of an analyte present in the subject's blood stream or present within another bodily fluid. The sensor can be electrochemical or non-electrochemical. In one aspect, the sensor is electrochemical. Optionally, the electrochemical sensor includes at least one electrode, for example a working electrode; however any combination of working electrode(s), reference electrode(s), and/or counter electrode(s) can be implemented. Optionally, the sensor includes at least one exposed electroactive area (e.g., working electrode), a membrane system (e.g., including an enzyme), a reference electrode (proximal to or remote from the working electrode), and an insulator material.

In some embodiments, the sensor is configured to measure one or more analytes. In other embodiments, the sensor is configured to measure at least glucose concentration. A glucose sensor for use with the sensor system can be configured to utilize a variety of analyte sensors including a variety of measurement technologies, such as enzymatic, chemical, physical, electrochemical, spectrophotometric, polarimetric, calorimetric, radiometric, and the like.

Glucose is only one example analyte that can be sensed. The term "analyte" as used herein is a broad term and refers, without limitation, to a substance or chemical constituent in a biological fluid (for example, blood, interstitial fluid, cerebral spinal fluid, lymph fluid or urine) that can be analyzed.

Analytes can include naturally occurring substances, artificial substances, metabolites, and/or reaction products. Optionally, the analyte for sensing and/or measurement is glucose. However, other analytes are contemplated as well, including but not limited to acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotimidase; biopterin; c-reactive protein; carnitine; carnosinase; CD4; ceruloplasmin; chenodeoxycholic acid; chloroquine; cholesterol; cholinesterase; conjugated 1-β hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, glucose-6-phosphate dehydrogenase, hemoglobin A, hemoglobin S. hemoglobin C, hemoglobin D, hemoglobin E, hemoglobin F, D-Punjab, beta-thalassemia, hepatitis B virus, HCMV, HIV-1, HTLV-1, Leber hereditary optic neuropathy, MCAD, RNA, PKU, *Plasmodium* vivax, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free β-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; glucose-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase I; 17-alpha-hydroxyprogesterone; hypoxanthine phosphoribosyl transferase; immunoreactive trypsin; lactate; lead; lipoproteins ((a), B/A-1, β); lysozyme; mefloquine; netilmicin; phenobarbitone; phenyloin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, *Dracunculus medinensis*, *Echinococcus granulosus, Entamoeba histolytica*, enterovirus, *Giardia duodenalisa, Helicobacter pylori*, hepatitis B virus, herpes virus, HIV-1, IgE (atopic disease), influenza virus, *Leishmania donovani*, leptospira, measles/mumps/rubella, *Mycobacterium leprae, Mycoplasma pneumoniae,* Myoglobin, *Onchocerca volvulus*, parainfluenza virus, *Plasmodium falciparum*, poliovirus, *Pseudomonas aeruginosa,* respiratory syncytial virus, rickettsia (scrub typhus), *Schistosoma mansoni, Toxoplasma gondii, Trepenoma pallidium, Trypanosoma cruzi/rangeli,* vesicular stomatis virus, *Wuchereria bancrofti,* yellow fever virus); specific antigens (hepatitis B virus, HIV-1); succinylacetone; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; and zinc protoporphyrin.

Salts, sugar, protein, fat, vitamins, and hormones naturally occurring in blood or interstitial fluids can also constitute analytes.

The analyte detected and/or measured can be naturally present in the biological fluid, for example, a metabolic product, a hormone, an antigen, an antibody, and the like. Alternatively, the analyte can be introduced into the body, for example, a contrast agent for imaging, a radioisotope, a chemical agent, a fluorocarbon-based synthetic blood, or a drug or pharmaceutical composition, including but not limited to insulin; ethanol; cannabis (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbituates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body can also be analyzed, such as, for example, ascorbic acid, uric acid, dopamine, noradrenaline, 3-methoxytyramine (3MT), 3,4-dihydroxyphenylacetic acid (DOPAC), homovanillic acid (HVA), 5-hydroxytryptamine (5HT), histamine, Advanced Glycation End Products (AGEs) and 5-hydroxyindoleacetic acid (FHIAA).

In one embodiment, the sensing system 100 is configured for repetitive or cyclic sensing and measurements of sample analyte concentration. Alternatively, only one sample measurement is taken. In some embodiments, a plurality of sample measurements are taken, such as from about 2 to about 50 or more measurements and/or at a predetermined sample rate. In one aspect, a sampling rate of between about 1 measurement per second and about 1 measurement per minute can be used. Optionally, the rate is from about 1 measurement per 2 seconds to about 1 measurement per 30 seconds. Optionally, sample measurements are taken substantially continuously, such as but not limited to substantially intermittently, as described elsewhere herein. Signals and/or data manipulation from the sensor can be used while the sensor system is in the first or second configuration to determine an appropriate time interval for the sensor in the sample paths or calibration path. Such methods include for example, waveform analysis, sensor sensitivity, and/or signal intensity.

Referring now to FIG. 2 and to FIG. 3B, in the advanced, second sensor configuration, the valve 104 seals about at least a portion of the sensor apparatus 103. By sealing about a least a portion of the sensor apparatus, the valve impedes the exchange of fluids between the sample path 108 and the calibration path 110 when the sensor is positioned in the lumen of the sample path. In this second configuration, sampling can proceed and optionally, flushing of the sample path can proceed without contamination by fluids contained in the calibration path. Moreover, the isolation of the fluid pathways while the sensor is positioned in the lumen of the sample path prevents substantial administration of fluid contained in the calibration path to the subject during the sensing protocol.

Since the valve 104 also impedes flow of fluids between the two pathways when the sensor is positioned in the calibration path 110, substantial administration of fluids in the calibration pathway to the subject is reduced or prevented during sensing and calibration protocols and during cycling between the sensing and calibration protocols. Thus, sensing and calibration can be effectively repeated without substantial administration of fluids in the calibration fluid path to the subject.

Figure 3C:
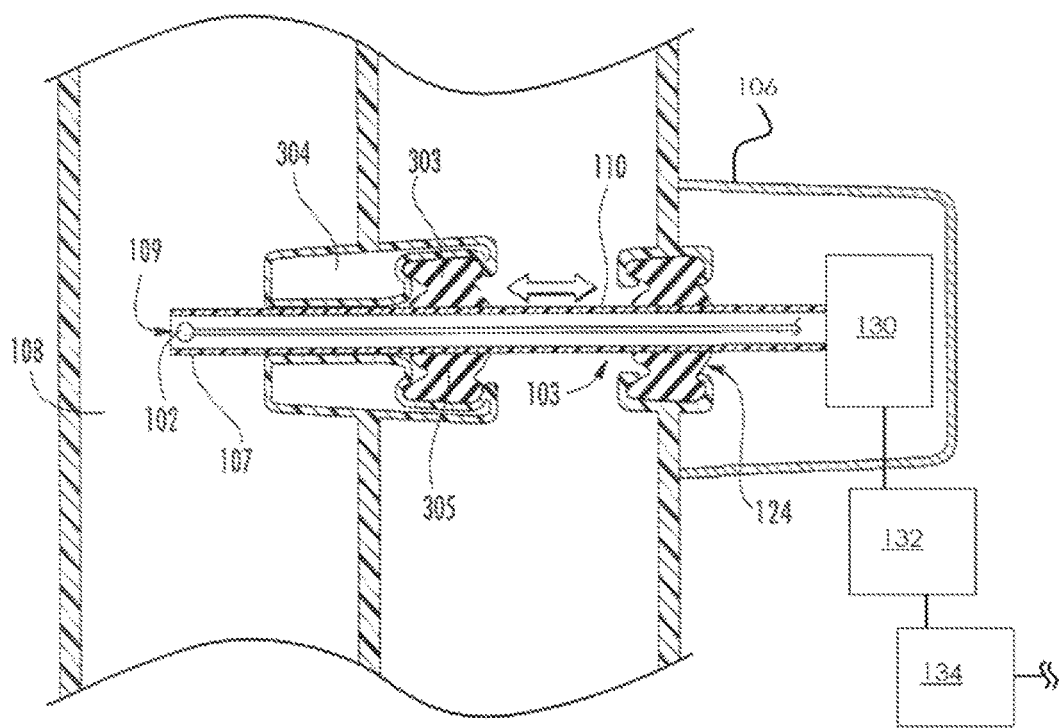
FIGS. 3C and 3D are schematic cross sectional illustrations advancing and retracting portions of the example sensor system of FIG. 2 between the calibration path and sample path.
Figure 3D:
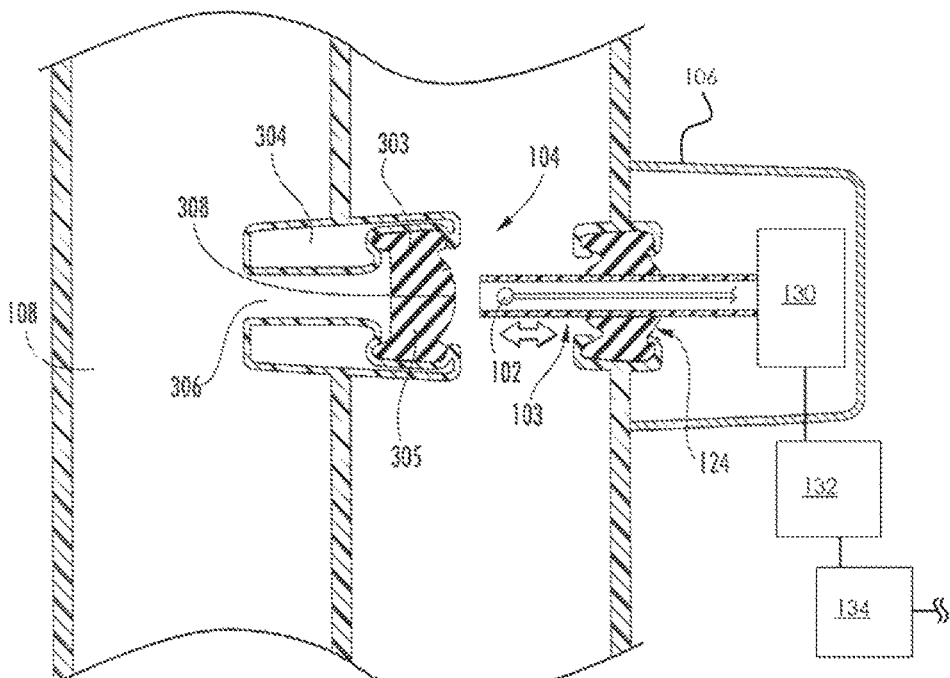

With reference to FIGS. 3C and 3D, exemplary components configured to advance and retract the sensor apparatus 103 and the sensor 102 between the calibration path 110 and the sample path 108, are illustrated. Thus, actuator 130, which includes linear actuators, solenoids, piezo-electric switches, magnets, worm gears and the like coupled to the conduit 107 to provide bidirectional (up/down) motion. Other examples of actuators can be used that can advance and retract the sensor between the lumen of the calibration path 110 and the sample path 108. Actuator 130 can be coupled to a motor 132, for example, a piezo-driven motor, or other common DC motor, which can be connected to a controller 134 and/or other control means as further disclosed below. In one example, a worm gear is cooperatively coupled to the outer surface of sensor apparatus 103, the worm gear configured to displace the apparatus a predetermined distance in a forward/backward direction that includes entry and exit from the sample path 108 to calibration path 110 through the valve 124. In another example a solenoid is configured at a distal end of the sensor apparatus to drive the apparatus upon receiving a signal from the controller 134 in a forward/backward direction that includes entry and exit from the sample path 108 to calibration path 110 through the valve 124. While the sensor apparatus 103 and sensor 102 are shown in FIGS. 3A-3D as essentially perpendicular to the respective longitudinal axis of the calibration path 110 and the sample path 108, in other embodiments, the sensor apparatus 103 and sensor 102 can be angled to minimize or reduce disturbance of the flow of fluid in the respective paths. Thus, in one aspect, the sensor apparatus 103 and sensor 102 can be angled relative to the longitudinal axis of the calibration path 110 and the sample path 108 between about 10 degrees to less than 90 degrees.

The sensor apparatus can further comprise a housing 106 to contain the actuator 130 and/or a portion of the sensor 102 and/or sensor apparatus 103, which is fluidly sealed from the calibration flow path by a valve 124. Portions of the sensor apparatus, such as the conduit, can be slidably advanced and retracted through the valve 124 to position at least a portion of the sensor in either the calibration path 110 or the sample path 108. In one aspect, forward/backward directional motion of the sensor apparatus 103 that includes entry and exit from the sample path 108 to calibration path 110 is manually controlled by the user, for example, housing 106 can be elastomeric dome or button sealed about calibration path 110 or the valve 124, and upon depressing the housing, the sensor is driven from the calibration path 110 into the sample path 108, while releasing the housing causes the sensor apparatus to withdraw from the sample path 108 into calibration path 110.

The sensor system can further comprise a processing system 126 that can comprise at least one processor. The processing system can be used to initiate, coordinate and complete sensing and calibration protocols. The processing system can also be used to process data obtained with the sensor 102. Such processing can include determination of the presence and/or levels of a sensed analyte of the bodily fluid of the subject. For example, the sensor can detect glucose and glucose detection data from the sensor can be communicated to the processing system 126. The processing system can use the communicated glucose detection data to determine and indicate to a user that glucose is present in the bodily fluid.

Moreover, the processing system can determine the level or concentration of glucose in the sample at a given time, at multiple times, or in real time for one or more sensing events in the sample path. The processing system can be further configured to control the actuator system, and optionally, the valve 112, and the processing system, alone or in combination with the controller 134, can therefore be used to advance or retract the sensor into a desired path, to draw a bodily fluid into the sample path, and/or to infuse the sample path with infusion fluid, depending on a programmed sensing and calibration protocol. The processing system can also be configured to control the regulation of fluid flow by valves 120 and 122. Therefore the processing system 126 can be used to implement sensing and calibration protocols with the described sensor system, provide for error analysis, alarm, etc.

The electronics associated with the sensor system can include a processor module that includes the central control unit that controls the processing of the integrated sensor system. Optionally, the processor module includes a microprocessor; however, a computer system other than a microprocessor can be used to process data. For example, an ASIC can be used for some or all of the sensor's central processing. The processor provides semi-permanent storage of data, for example, storing data such as sensor identifier (ID) and programming to process data streams (for example, programming for data smoothing and/or replacement of signal artifacts). The processor additionally can be used for the system's cache memory, for example for temporarily storing recent sensor data. In some embodiments, the processor module comprises memory storage components such as ROM, RAM, dynamic-RAM, static-RAM, non-static RAM, EEPROM, rewritable ROMs, flash memory, and the like.

In another example sensor system, the sensor apparatus is not selectively moveable between a position in the calibration path and the sample path. Instead, the sensor remains housed in the calibration path. In this example system, bodily fluid can be drawn up into the sample path and then redirected into the calibration path through a valve, which can be valve 103. The valve can impede flow of fluid between the sample path and the calibration path and can selectively allow passage of a bodily fluid sample into the calibration path. In the calibration path, the sensor can contact the bodily fluid. Subsequent to contacting the sensor, the bodily fluid can be returned to the sample path through a second valve which also generally impedes flow between the sample and calibration paths. Thus, similar to the first valve, the second valve can selectively allow flow of bodily fluid between the calibration and sample paths. Once the bodily fluid is returned to the sample path, it can be flushed back into the subject. Moreover, calibration fluid can be introduced into the calibration path to calibrate the sensor. The calibration fluid does not substantially pass into the sample path so that the volume of calibration fluid administered to the subject is reduced.

Many modifications and other embodiments of the invention set forth herein will come to mind to one skilled in the art to which this invention pertains having the benefit of the teachings presented in the foregoing description. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A sensor system, comprising:
    a calibration path configured for fluid communication with a first fluid;
    a first valve fluidically coupled to the calibration path;
    a sample path isolated from the calibration path, the sample path adapted to be placed in fluid communication with a bodily fluid of a subject and configured to accept at least a portion of the bodily fluid into the sample path,
    a second valve fluidically coupling the sample path and the calibration path;
    a sensor apparatus comprising: a sensor, wherein the sensor is configured to sense at least one analyte in the bodily fluid, wherein the sensor is coupled with the first valve and reversibly moveable between a first configuration wherein at least a portion of the sensor is located in the calibration path and a second configuration wherein at least a portion of the sensor is extended from the first valve through the second valve into the sample path; and
    an actuator and a processing device in operative communication with the actuator, the processing device configured to implement activation of the actuator to move the sensor between its position in the calibration path and its position in the sample path.

2. The sensor system of claim 1, wherein the first valve is aligned with the second valve along a longitudinal axis of the sensor for guiding reversible movement of at least a portion of the sensor between the calibration path and the sample path.

3. The sensor system of claim 1, wherein the second valve impedes flow of the first fluid into the sample path.

4. The sensor system of claim 1, wherein the second valve impedes flow of bodily fluid into the calibration path.

5. The sensor system of claim 1, wherein the second valve comprises a resealable aperture.

6. The sensor system of claim 5, wherein the at least a portion of the sensor apparatus received by the second valve resealable aperture in the second configuration.

7. The sensor system of claim 6, wherein the second valve seals about at least a portion of the sensor apparatus.

8. The sensor system of claim 1, further comprising a flow control device configured to regulate flow of biological fluid within the sample path.

9. The sensor system of claim 8, wherein the sample path is further in fluid communication with an infusion fluid source comprising an infusion fluid.

10. The sensor system of claim 9, wherein the flow control device is further configured to regulate flow of infusion fluid within the sample path.

11. The sensor system of claim 10, wherein the flow control device comprises a flow regulating device selected from the group consisting of a valve, cam, and pump.

12. The sensor system of claim 11, wherein the valve is a pinch valve.

13. The sensor system of claim 11, wherein the pump is selected from the group consisting of a volumetric infusion pump, a peristaltic pump, a piston pump and a syringe pump.

14. The sensor system of claim 9, wherein the flow control device is operatively positioned between the sensor and the infusion fluid source.

15. The sensor system of claim 14, wherein the flow control device is selectively activatable to draw bodily fluid from the subject, along at least a portion of the sample path and into contact with the sensor when the sensor is positioned within the sample path.

16. The sensor system of claim 15, wherein the flow control device is selectively activateable to allow flow of infusion fluid through the sample path.

17. The sensor system of claim 15, wherein the sensor is a glucose sensor.

18. The sensor system of claim 17, wherein the bodily fluid is blood and where the glucose sensor is configured to sense glucose in the blood.

19. The sensor system of claim 1, wherein the actuator comprises a motor or a solenoid.

20. The sensor system of claim 1, wherein the first fluid is a calibration fluid.

21. The sensor system of claim 20, wherein the calibration path is in fluid communication with a second fluid source that does not comprise calibrant.

22. The sensor system of claim 21, wherein the first fluid and the second fluid source are mixed in the calibration path.

23. The sensor system of claim 22, wherein the sensor is positioned in the mixed calibration fluid and second fluid source while in the first configuration.

24. The sensor system of claim 1, wherein the first fluid source comprises an anticoagulant.

25. A method for sensing one or more analytes in a bodily fluid of a subject, comprising: positioning an analyte sensor in a first configuration wherein the analyte sensor is positioned in a second valve fluidically coupled to a sample path, the sample path configured in fluid communication with the bodily fluid of the subject, the bodily fluid comprising the one or more analytes;

drawing a volume of the bodily fluid into the sample path such that the analyte sensor contacts the bodily fluid and senses the one or more analytes;

positioning the analyte sensor in a second configuration, wherein the analyte sensor is received in a first valve fluidically coupled to a calibration path, the calibration path configured to receive a first fluid;

wherein the analyte sensor comprises an actuator, the actuator configured to position at least a portion of the analyte sensor in the calibration path in the first configuration, and to position at least a portion of the analyte sensor in the sample path in the second configuration by reversibly extending the analyte sensor from the first valve and through the second valve; and wherein the second valve fluidically couples the sample path and the calibration path.

26. The method of claim 25, wherein the first fluid comprises at least one calibrant, the method further comprising calibrating the sensor by contacting the sensor while positioned in the calibration path with the first fluid.

27. The method of claim 25, wherein the first fluid comprises a flush solution, the method further comprising flushing the sensor by contacting the sensor while positioned in the calibration path with the first fluid.

28. The method of claim 25, wherein the sample path is physically isolated from the calibration path.

29. The method of claim 25, wherein the bodily fluid comprises blood.

30. The method of claim 25, wherein the first fluid comprises an anticoagulant.

* * * * *